United States Patent
Chou et al.

(10) Patent No.: US 6,825,379 B2
(45) Date of Patent: Nov. 30, 2004

(54) METHOD FOR RECOVERING AND PRODUCING $C_4$-$C_6$ DICARBOXYLATE FROM ALKALINE WASTE SOLUTION GENERATED IN CAPROLACTAM PREPARATION PROCESS

(75) Inventors: Sien-Chun Chou, Taipei (TW); Edward K. S. Wang, Taipei (TW); Chung Ho Wu, Taipei (TW); Yaw Jong Liu, Taipei (TW); Ping Chiang, Taipei (TW)

(73) Assignee: Chemaxz International Corporation (TW)

( * ) Notice: Subject to any disclaimer, the term of this patent is extended or adjusted under 35 U.S.C. 154(b) by 41 days.

(21) Appl. No.: 10/047,835

(22) Filed: Jan. 14, 2002

(65) Prior Publication Data

US 2003/0045750 A1 Mar. 6, 2003

(30) Foreign Application Priority Data

Aug. 14, 2001 (TW) ........................................ 90119851 A

(51) Int. Cl.$^7$ .......................... C07C 67/48; C07C 51/16; B01D 3/34
(52) U.S. Cl. ...................... 562/524; 560/191; 560/179; 560/193; 560/204; 203/35

(58) Field of Search ................................. 560/179, 191, 560/193, 204; 562/524; 203/35

(56) References Cited

U.S. PATENT DOCUMENTS

| | | | |
|---|---|---|---|
| 4,052,441 A | 10/1977 | Brunner | 560/179 |
| 4,271,315 A | 6/1981 | Cywinski | 560/204 |
| 4,316,775 A | 2/1982 | Nash | 203/43 |
| 4,442,303 A | 4/1984 | Mims | 560/191 |
| 6,063,958 A | 5/2000 | Chen et al. | 562/580 |

*Primary Examiner*—Ba K. Trinh
*Assistant Examiner*—Taylor V Oh
(74) *Attorney, Agent, or Firm*—Peter F. Corless; John B. Alexander; Edwards & Angell, LLP

(57) ABSTRACT

The present invention relates to a method for recovering and producing $C_4$–$C_6$ dicarboxylates from an alkaline waste solution generated in a caprolactam preparation process, in which the alkaline waste solution is treated with sulfuric acid to separate into an aqueous phase and an organic phase, allowing valuable substances contained in the organic phase to be firstly oxidized and converted into dicarboxylic acids. The dicarboxylic acids then undergo concentration, esterification and distillation processes, so as to obtain desirable $C_4$–$C_6$ dicarboxylates with high purity. This therefore provides an efficient and improved method for effectively recovering most valuable substances from the alkaline waste solution, so that economic benefits in recovery are greatly raised.

16 Claims, 1 Drawing Sheet

METHOD FOR RECOVERING AND PRODUCING $C_4$-$C_6$ DICARBOXYLATE FROM ALKALINE WASTE SOLUTION GENERATED IN CAPROLACTAM PREPARATION PROCESS

FIELD OF THE INVENTION

The present invention relates to methods for producing $C_4$–$C_6$ dicarboxylates, and more particularly, to a simple and efficient method for recovering and producing $C_4$–$C_6$ dicarboxylates from an alkaline waste solution generated in a caprolactam preparation process.

BACKGROUND OF THE INVENTION

To prepare cyclohexanol and cyclohexanone by oxidizing cyclohexane with air in liquid phase plays an important role in fiber industry such as synthesis of nylon 6 & 66 etc. For example, caprolactam used as raw material of nylon 6 and adipic acid used as raw material of nylon 66, are both made from cyclohexanol and cyclohexanone.

In a process for preparing caprolactam, normally, cyclohexane is introduced with air and oxidized to generate cyclohexanol and cyclohexanone at a temperature 150–160° C. and under a pressure 8–10 kg/cm$^2$ in the presence of Co or Cr used as a catalyst. The generated cyclohexanol and cyclohexanone are further treated with subsequent processes such as oximation and Beckmann rearrangement, so as to synthesize caprolactam.

During cyclohexane oxidation, part of cyclohexane may be over-oxidized to produce some neutral substances and acidic substances that would react with neutral alcohols to form esters. Accordingly, besides main products i.e. cyclohexanol and cyclohexanone, by-products such as monocarboxylic acids, dicarboxylic acids (mainly including succinic acid, glutaric acid and adipic acid), oxycarboxylic acids, a small amount of alcohols, aldehyde, low molecular weight esters, esters containing cyclohexanol group, ketones and other unknown organic substances, also co-exist with the main products in the oxidation reaction mixture. To isolate these by-products from cyclohexanol and cyclohexanone, is usually done by saponifying and salinizing the by-products with an aqueous solution of sodium hydroxide to form an aqueous solution of organic acid salts of sodium, which is called an alkaline waste solution.

Salts of dicarboxylic acids (such as succinic acid, glutaric acid, adipic acid, etc) contained in the alkaline waste solution, are acidified and separated to form various dicarboxylic acids of succinic acid, glutaric acid and adipic acid, which dicarboxylic acids can be further esterified with methanol or other alcohols to synthesis dicarboxylates of great applicability in industry. For example, $C_4$–$C_6$ dicarboxylic acids are esterified with methanol to form a mixture of dimethyl dicarboxylates, which is a non-toxic environmental-friendly organic solvent with high efficiency, high burning point and great solubility solvency, and thus may be potentially commercialized in the market. Besides, dimethyl adipate can be converted by esterification/hydrogenation into 1,6-hexanediol, which is an important raw material of polyurethane resin and polyester resin, and thereby endowed with high commercial and economic value.

Conventionally, the alkaline waste solution is directly burnt and converted into sodium carbonate, so as to recover sodium contained in the alkaline waste solution. Although this treatment is simply direct, highly corrosive alkaline substances are usually produced in combustion, thereby undesirably damaging the equipment lifetime with safety concern. Also, carbon dioxide produced from combustion brings about environmental problems such as green house effect and air pollution, etc. Further, it is a significant loss of economic benefits if not capable of recovering valuable substances from the alkaline waste solution. In view of the above, associated patents disclosing recovery of valuable substances from an alkaline waste solution, are exemplified as follows.

In U.S. Pat. No. 6,063,958, an alkaline waste solution produced from a caprolactam preparation process, is firstly neutralized with a proton-containing aqueous solution of inorganic acids, for adjusting its pH value to less than or equal to 3 and separating the alkaline waste solution into an organic phase and an aqueous phase. The aqueous phase is an aqueous solution of inorganic acid salts e.g. sodium sulfate etc. The organic phase is extracted for adipic acid and 6-hydroxycaproic acid therefrom by using a proton-containing aqueous solution of inorganic acids, allowing the organic phase to be separated into layers, an aqueous layer of which is further extracted for adipic acid and 6-hydroxycaproic acid by using alcohols, ketones, esters or a mixture of any two thereof. The above-obtained extract is then adopted to extract the aqueous phase containing inorganic acid salts e.g. sodium sulfate, for retrieving adipic acid and 6-hydroxycaproic acid. As a result, the final extract is alcohols, ketones, esters or the mixture of any two thereof, with rich content of adipic acid and 6-hydroxycaproic acid. By distilling this final extract, valuable substances e.g. adipic acid and 6-hydroxycaproic acid are recovered at a yield of 50–55%.

Japan Patent Publication Sho 53-33567 discloses addition of sodium hydroxide to a reaction solution of cyclohexane oxidation. The obtained alkaline organic solution is then neutralized and adjusted its pH value with sulfuric acid, and separated into an organic phase and an aqueous phase of a sodium sulfate solution. The organic phase is firstly extracted with an inorganic solution containing sodium sulfate at concentration of 15% or more by weight. The extract is mixed with the aqueous phase, and then the mixture is extracted with an organic solvent. Such resulted extract is subsequently distilled for removing the organic solvent therefrom, so as to proceed esterification/hydrogenation for producing 1,6-hexanediol.

U.S. Pat. No. 4,442,303 discloses a method for recovering $C_4$–$C_6$ dicarboxylic acids from an aqueous waste solution generated in a process of adipic acid preparation. A mixture of $C_1$–$C_3$ alkyl alcohols and $C_6$–$C_{20}$ alkyl alcohols is mixed and esterified with the aqueous waste solution. After the reaction mixture is settled to form separate phases, an organic phase thereof is distilled to obtain $C_4$–$C_6$ dicarboxylic acids and esters containing $C_6$–$C_{20}$ alkyl alcohols, so as to recover the dicarboxylic acids.

U.S. Pat. No. 4,052,441 discloses that a reaction mixture obtained by catalyzing cyclohexane with air, is added with an alkaline solution to separate out an alkaline waste solution containing monocarboxylic acids, 6-hydroxycaproic acids and dicarboxylic acids. The alkaline waste solution is neutralized with sulfuric acid to separate into an organic phase of organic acids and an aqueous phase of a sodium sulfate solution. The organic phase is distilled under vacuum for removing monocarboxylic acids with low boiling point and water, and then cooled down to recover adipic acid by crystallization. After crystallization, the parent liquor is treated with two-step distillation for respectively recovering monocarboxylic acids, 6-hydroxycaproic acid and dicarboxylic acids, which can be esterified and fractionated to get ester products. The crude adipic acid obtained from crystallization can be further purified by recrystallization or esterification.

U.S. Pat. Nos. 4,271,315 and 4,316,775 disclose a method for recovering a waste solution generated in a process of adipic acid preparation. First, the waste solution is concentrated to remove part of water and volatile substances. Then, the concentrate is esterified with methanol, and subsequently extracted for extracting $C_4$–$C_6$ dimethyl dicarboxylates by using an insoluble organic solvent. After settling down, an organic phase is distilled for recovering the organic solvent, so as to obtain a mixture of $C_4$–$C_6$ dimethyl dicarboxylates.

Though the above patents provide useful methods or treatments, there are still some drawbacks in respect of recovering valuable substances as follows.

1. Extraction of valuable substances is performed by using soluble or insoluble solvents as extract agents, which extraction process is complex in proceeding, and low in total recovery yield of the valuable substances (below 50%), wherein the recovered valuable substances still contain a lot of impurities e.g. organic residues that need to be burnt or treated for removal, so that only part of the valuable substances are recovered.
2. Dicarboxylic acids recovered by crystallization mainly include adipic acid, which is low in recovery yield and purity, and thereby needs to be treated with multiple recrystallization for achieving desirable purity; whereas other valuable substances such as 6-hydroxycaproic acid and other dicarboxylic acids are unable to be recovered.
3. Direct esterification of a waste solution with alcohols can only recover some dicarboxylic acids. For example, 6-hydroxycaproic acids having hydroxyl group only form monoesters that cannot be combined with dicarboxylates for sale.

Besides adipic acid and 6-hydroxyccaproic acid, the waste solution also contains 20–40% low molecular weight ester compounds, e.g. valuable substances such as incompletely saponified esters or ketones containing cyclohexanol group and some $C_4$–$C_6$ lactones. If these compounds are not oxidized and converted into useful dicarboxylic acids, it results in accumulation of organic residues and decrease in a recovered amount of dicarboxylic acids. Thus, a method for recovering a waste solution generated in a process of adipic acid preparation, is not applicable to recovery of valuable substances from an alkaline waste solution produced in a caprolactam preparation process.

SUMMARY OF THE INVENTION

In response to the above drawbacks, the present inventor has researched to find out a simple and efficient method for recovering valuable substances from an alkaline waste solution so as to produce dicarboxylates, in which highly efficient oxidation and improved concentration are adopted to efficiently recover most valuable substances present in the alkaline waste solution, thereby significantly increasing economic benefits in recovery.

Therefore, a primary objective of the present invention is to provide a method for recovering and producing $C_4$–$C_6$ dicarboxylates from an alkaline waste solution generated in a caprolactam preparation process, which can efficiently recover most valuable substances present in the alkaline waste solution.

In a process of caprolactam production, crude products obtained from cyclohexane oxidation are saponified and salinized, and extracted with water to separate into two phases including an organic phase and an aqueous phase. The organic phase is a mixture of cyclohexanol and cyclohexanone, and the aqueous layer is so-called alkaline waste solution sodium containing sodium salt of organic acids. The alkaline waste solution is neutralized and adjusted for its pH value with sulfuric acid, so as to separate into an aqueous layer and an organic layer. The aqueous layer mainly comprising sodium sulfate, is delivered to a manufactory for recovering sodium sulfate. The organic layer contains valuable substances approximately including: formic acid 1–3%, acetic acid 1–3%, butyric acid 2–5%, valeric acid 0.1–0.5%, caproic acid 2–6%, succinic acid 0.05–0.3%, glutaric acid 0.5–1.5%, adiptic acid 8–15%, 6-hydroxycaproic acid 10–20%, water 20–30%, and other compounds 20–40% e.g. low molecular weight ester compounds such as incompletely saponified esters or ketones containing cyclohexanol group, some $C_4$–$C_6$ lactones, and unknown organic substances. This organic layer is therefore where valuable substances are to be recovered by using the recovery method of the invention.

The method for recovering and producing $C_4$–$C_6$ dicarboxylates from an alkaline waste solution generated in a caprolactam preparation process of the invention, comprises the following steps.

(1) Oxidation and conversion of valuable substances present in an organic phase:

First, neutralize an alkaline waste solution generated by oxidizing cyclohexane in a caprolactam preparation process, with sulfuric acid to adjusted its pH value and separate it into an aqueous phase and an organic phase. Add nitric acid as an oxidant to the organic phase, and proceed oxidation and conversion at suitable reaction stages under suitable temperature and pressure, so as to oxidize and convert most valuable substances present in the organic into dicarboxylic acids.

(2) Two-stage concentration of the reaction mixture after oxidation and conversion:

Introduce the reaction mixture obtained in the step (1) by oxidation and conversion with nitric acid into a two-stage concentration apparatus. The first-stage concentration is to distill out low boiling-point monocarboxylic acids and most nitric acid. In the second-stage concentration, remaining nitric acid and nitrocompounds are decomposed at higher temperature to recover most nitric acid, and thus crude concentrates mainly comprising $C_4$–$C_6$ dicarboxylic acids are obtained.

(3) Esterification of crude concentrates of dicarboxylic acids:

Place the crude concentrates of $C_4$–$C_6$ dicarboxylic acids obtained in the step (2) into an esterification apparatus, and add $C_1$–$C_4$ alkyl alcohols to proceed esterification with or without a catalyst. In order to desirably achieve sufficient esterification, two-stage esterification is performed. The first-stage esterification is conducted at lower temperature and pressure to get intermediates with better fluidity, which intermediates are produced by half of carboxylic acid groups being esterified. Subsequently, the second-stage esterification is performed at higher temperature and pressure, allowing esterification to be sufficiently proceeded, so as to obtain highly esterified crude dicarboxylates.

(4) Distillation of dicarboxylates:

Introduce the crude dicarboxylates obtained in the step (3) into at least one set of fractionation or distillation tower, so as to produce single-species dicarboxylates or a mixture of at least two species of dicarboxylates.

DETAIL DESCRIPTION OF THE PREFERRED EMBODIMENTS

Figure 1:
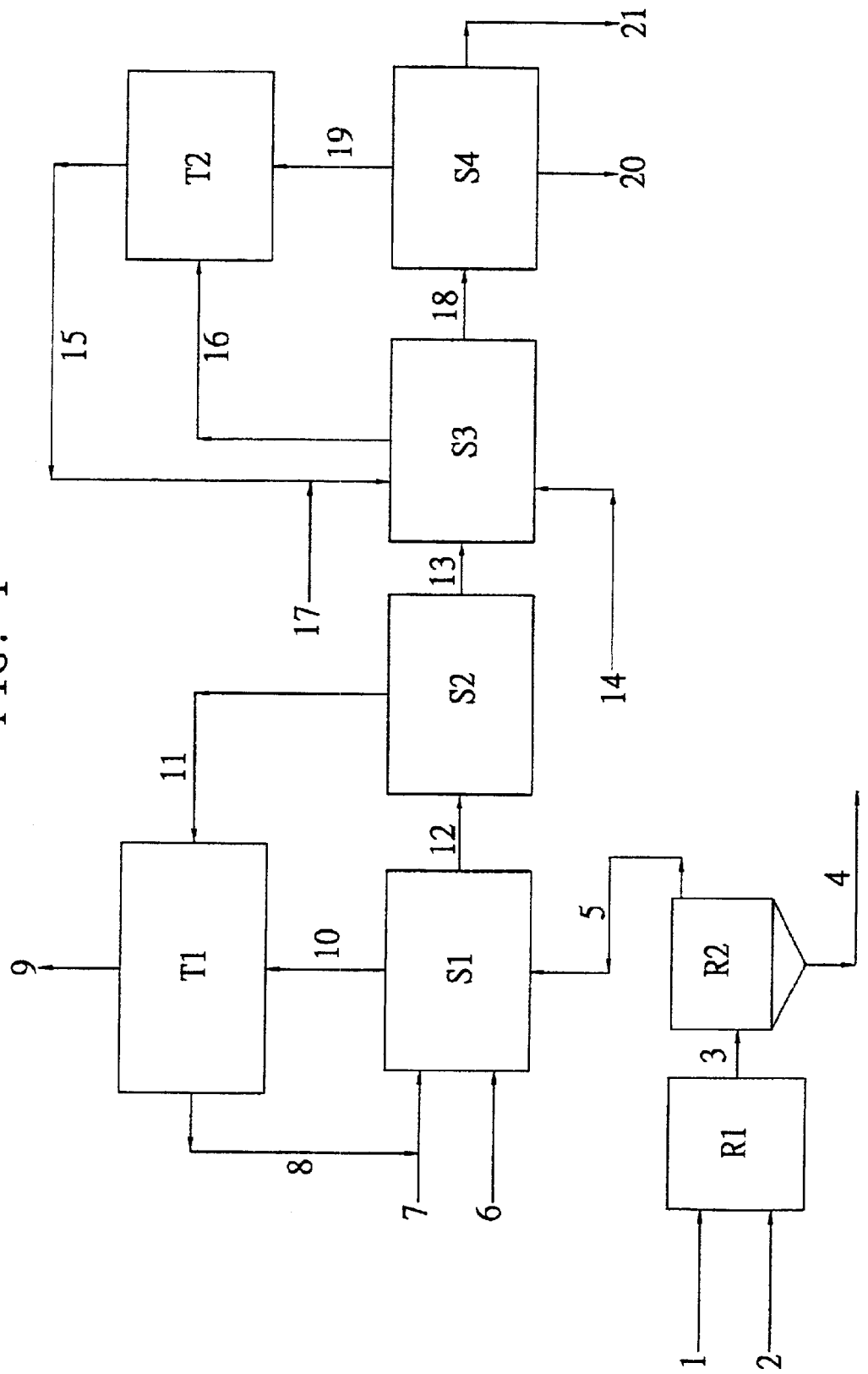
FIG. 1 is a schematic flowchart showing a method for recovering and producing $C_4$–$C_6$ dicarboxylates from an alkaline waste solution generated in a caprolactam preparation process of the present invention.

The following description is made to further detail a method for recovering and producing $C_4$–$C_6$ dicarboxylates from an alkaline waste solution generated in a caprolactam preparation process of the present invention.

In step (1), an alkaline waste solution produced from cyclohexane oxidation in a caprolactani preparation process is first neutralized and adjusted for its pH value with sulfuric acid to separate into an organic phase and an aqueous phase. The aqueous phase containing mainly sodium sulfate is delivered to a manufactory for recovering sodium sulfate. The organic phase contains valuable substances e.g. adipic acid, 6-hydroxycaproic acid, and other low molecular weight ester compounds such as incompletely saponified esters or ketones of cyclohexanol group, and $C_4$–$C_6$ lactones, etc. This is mainly purposed to completely convert 6-hydroxycaproic acid present at 10–20% in the organic phase into adipic acid, and to properly oxidize other low molecular weight esters into dicarboxylic acids. Consequently, content of dicarboxylic acids in the oxidized solution is greatly increased, thereby desirably enhancing the recovery efficiency. In order to recover more dicarboxylic acids for producing dicarboxylates, besides nitric acid, one or more additional oxidant can be utilized, such as hydrogen peroxide, perchloric acid and potassium permanganate, to oxidize and convert valuable substances of the organic phase at suitable temperature and pressure. Nitric acid used herein is generally at concentration of 10–90%, preferably 20–40%. In order to achieve full reaction, a ratio of nitric acid to the organic phase is 0.5–30:1 by weight, preferably 5–10:1. Other oxidants added in purpose of enhancing oxidation efficiency, are in a ratio of 0–5% relative to nitric acid by weight, preferably 0.01–1%. Reaction is performed in condition of at least one stage, preferably 2–5 stages, with variable reaction temperature and time in different stages. Reaction ternpcrature is ranged between 10–150° C., preferably 30–20° C., and gradually increases from the first to the last reaction stage with an interval difference between 5–30° C., preferably 10–20° C. Reaction time in each reaction stage is usually from 5 minutes to four hours, preferably 10 minutes to two hours. Reaction pressure is absolute pressure of 0.5–2 kg/cm$^2$, preferably 0.8–1.2 kg/cm$^2$. NO(g) and NO$_2$(g) produced in the reaction are delivered to a nitric acid recycle system for recovery.

In step (2), the reaction mixture obtained in the step (1) by oxidation and conversion with nitric acid, is introduced into a two-stage concentration apparatus. The first-stage concentration is controlled at temperature of 50–120° C., preferably 80–100° C., and under pressure from vacuum to ambient pressure, which is usually absolute pressure of 0.2–1.2 kg/cm$^2$, preferably 0.8–1.2 kg/cm$^2$. Stream stripping may also be applied to the first-stage concentration for achieving better concentration effect. The second-stage concentration is controlled at temperature of 120–200° C., preferably 100–120° C., and under absolute pressure of 0.5–2.0 kg/cm$^2$, preferably 0.8–1.5 kg/cm$^2$. Concentration performed with two stages is a characteristic feature of the invention. The reason is that, nitric acid may react with organic substances to form complicated nitrocompounds that cannot be easily distilled or steamed for removal, and remaining residues after distillation if containing nitrocompounds would detrimentally affect subsequent esterification reaction; therefore it needs to adopt the two-stage concentration process. In particular, the first-stage concentration allows most low boiling-point monocarboxylic acids to be distilled out, and the second-stage concentration decomposes remaining nitrocompounds for recovering nitric acid therefrom, so as to obtain crude concentrates mainly containing $C_4$–$C_6$ dicarboxylic acids.

In step (3), the crude concentrates of $C_4$–$C_6$ dicarboxylic acids obtained in the step (2) are placed into an esterification apparatus, with addition of $C_1$–$C_4$ alkyl alcohols such as methanol, ethanol, propanol and butanol etc. A ratio of alkyl alcohols to crude dicarboxylic acids is 1–15:1, preferably 1–5:1. And, a catalyst is added in an amount of 0–5%, preferably 0.1–1% for proceeding esterification, which catalyst can be sulfuric acid, phosphoric acid, nitric acid, alkanesulfonic acid or benzenesulfonic acid, or cation-exchange resin etc. In order to achieve sufficient esterification, two-stage esterification is performed. The first-stage esterification is maintained at lower temperature and lower pressure, so as to obtain intermediates with better fluidity, which intermediates are produced by half of carboxylic acid groups being esterified, under temperature of 40–120° C., preferably 50–100° C., and absolute pressure 0.2–1.2 kg/cm$^2$, preferably 0.8–1.0 kg/cm$^2$, with esterification time of 0.5–8 hours, preferably 1–4 hours. Subsequently, the second-stage esterification is performed at higher temperature and pressure for allowing esterification to be fully proceeded, under temperature of 80–200° C., preferably 100–150° C., and absolute pressure 0.8–2.5 kg/cm$^2$, preferably 1.0–1.5 kg/cm$^2$, with esterification time of 0.5–8 hours, preferably 1–4 hours. Finally, highly esterified crude dicarboxylates are obtained at yield of 85% or more.

In step (4), the crude dicarboxylates obtained in the step (3) are introduced into at least one set of fractionation or distillation tower of a tray or packing type. By controlling number of trays and operation temperature and pressure, single-species dicarboxylates or a mixture of at least two species of dicarboxylates can be obtained. In order to produce a mixture of dicarboxylates for use as a solvent, theoretically, tray number is required at least 10–100, preferably 20–50; operation pressure is absolute pressure of 0.02–1.0 kg/cm$^2$, preferably 0.1–0.5 kg/cm$^2$; distillate collecting temperature is 70–250° C., preferably 100–150° C.

The above steps of the method for recovering and producing $C_4$–$C_6$ dicarboxylates from an alkaline waste solution generated in a caprolactam preparation process of the invention, can be illustrated with reference to FIG. 1.

First, in a process of caprolactam preparation, cyclohexane is oxidized in a liquid phase at temperature of 150–165° C. and under pressure of 8–10 atm in the presence of Co salt used as a catalyst. The obtained reaction mixture is basified by sodium hydroxide to obtain an alkaline waste solution 1 containing valuable substances such as adipic acid and 6-hydroxycaproic acid, etc. In an acidification tank R1, the alkaline waste solution 1 is neutralized with sulfuric acid 2, and the resulted reaction mixture 3 flows to a settlement tank R2 to separate into layers. A lower layer is an aqueous sodium sulfate solution 4, and an upper organic layer is an organic acid solution 5. The invention is characterized of recovering valuable substances from the organic acid solution 5.

The organic acid solution 5 of the organic layer is introduced into a nitric acid oxidation system S1. After fresh nitric acid 7 is mixed with recycled nitric acid 8 to achieve desired concentration, the obtained nitric acid together with a catalyst 6 are added to the nitric acid oxidation system S1, so as to proceed oxidation and conversion reactions for the organic acid solution 5 of the organic layer. Gases of monocarboxylic acids, NO, $NO_2$ and other gases 10 produced in the reactions are delivered to a nitric acid/monocarboxylic acid recycle system T1 for recovery.

An oxidized reaction mixture 12 generated from the nitric acid oxidation system S1, is then introduced into a two-stage concentration system S2, whereby crude concentrates 13 mainly containing $C_4$–$C_6$ dicarboxylic acids are obtained.

The crude concentrates of $C_4$–$C_6$ dicarboxylic acids 13 are then delivered to an esterification system S3, with addition of a mixture of $C_1$–$C_4$ alkyl alcohols 17 and alcohols 15 recycled from an alcohol recycle system T2, so as to proceed the esterification reaction in the presence of an added catalyst 14. The esterification system S3 is also performed in two stages, and generates highly esterified crude dicarboxylates 18. Water produced during esterification and non-reacted alcohols 16 are transferred to the alcohol recycle system T2 for alcohol recovery.

The crude dicarboxylates 18 are then moved to a distillation system S4 for fractionation and rectification. The distillation system $S_4$ consists of at least one set of fractionation or rectifying tower. By controlling number of trays in the tower and operation temperature and pressure, single-species dicarboxylates or a mixture of at least two species of dicarboxylates 21 can be obtained. Low boiling-point substances produced in distillation are delivered to the alcohol recycle system T2 for alcohol recovery.

EXAMPLE

The present invention will be described by using the following examples. It is to be understood that the scope of the invention is not limited to the disclosed examples. On the contrary, it is intended to cover various modifications and similar arrangements. The scope of the claims, therefore, should be accorded the broadest interpretation so as to encompass all such modifications and similar arrangements.

Example 1

Neutralize an alkaline waste solution generated from a caprolactam preparation process, and adjust its pH value to separate it into an aqueous phase and an organic phase containing valuable organic acids. Take 120 g of the organic phase as raw material of this example, and analyze its components as listed in Table 1.

TABLE 1

| Component | Wt. % | Weight of dicarboxylic acids (including 6-hydroxylcaproic acid) contained in 120 g raw material |
|---|---|---|
| Formic acid | 2.08% | |
| Acetic acid | 2.07% | |
| Butyric acid | 3.19% | |
| Valeric acid | 0.23% | |
| Caproic acid | 5.42% | |
| Succinic acid | 0.08% | 0.096 g |
| Glutaric acid | 0.85% | 1.02 g |
| Adipic acid | 10.15% | 12.18 g |
| 6-hydroxycaproic acid | 15.07% | 18.084 g |
| Water | 25.62% | |
| Others | 35.24% | |
| Total | 100% | 31.38 g |

Start to proceed a three-stage oxidation and conversion process. This process is conducted under ambient pressure in a batch-reaction manner. First, add 600 g of a 30% aqueous solution of nitric acid into a two-liter reaction bottle, and then gradually add 120 g of the organic phase into the reaction bottle with continuously stirring. In the meantime, a weight ratio of the organic phase to nitric acid is 1/5. Temperature of the first-stage reaction is maintained at 30° C. with material addition time of about 20 minutes. After the organic phase is completed added, the reaction is kept on for one more hour. Subsequently, raise reaction temperature to 50° C. and perform the second-stage reaction for another hour. Then, raise reaction temperature to 70° C. and perform the third-stage reaction for one more hour. This completes the overall oxidation and conversion reaction, which is followed by a concentration process.

Concentration is performed with a two-stage process. In the first-stage concentration, reaction temperature is up to around 120° C., for removing free nitric acid with introduction of steam. Then, stop steaming, and raise reaction temperature to 140° C. for proceeding the second-stage concentration, in which nitrocompounds are completely decomposed, and 61.5 g yield of crude concentrates mainly containing $C_4$–$C_6$ dicarboxylic acids are obtained, with components being analyzed as listed in Table 2.

TABLE 2

| Component | Wt. % | Weight of dicarboxylic acids (including 6-hydroxylcaproic acid) contained in 61.5 g crude concentrates |
|---|---|---|
| Formic acid | 0 | |
| Acetic acid | 0 | |
| Butyric acid | 0 | |
| Valeric acid | 0.29% | |
| Caproic acid | 0 | |
| Succinic acid | 14.27% | 8.78 g |
| Glutaric acid | 27.36% | 16.83 g |
| Adipic acid | 34.03% | 20.93 g |
| 6-hydroxycaproic acid | 0.53% | 0.33 g |
| Water | 0 | |
| $NO_3^-$ | 0.045% | |
| Others | 23.475% | |
| Total | 100% | 46.87 g |

Comparative Example 1

According to a method described in U.S. Pat. No. 6,063,958 through the use of the same start-up material as Example 1, the alkaline waste solution generated from the caprolactam preparation process is neutralized and adjusted for its pH value with sulfuric acid to separate into an aqueous phase of a sodium sulfate aqueous solution, and an organic phase containing valuable organic acids. Take 120 g of the organic phase and 370 g of the aqueous phase as raw material for this comparative example.

Extract 120 g of the organic phase at 70–80° C. with 600 g of an 18% aqueous sulfuric acid solution. Allow it to stand until separating into an upper layer (60 g) and a lower layer (660 g, solution A) containing valuable organic acids.

Extract 370 g of the aqueous phase of the aqueous sodium sulfate solution with 370 g of a solvent mixture of cyclohexanol and cyclohexanone at room temperature. Allow it to stand until separating into an upper layer (420 g, solution B) and a lower layer (420 g), which upper layer is an organic layer containing valuable organic acids and solvents.

Subsequently, extract solution A with solution B, and distill the extracted organic layer to remove solvent and obtain 7.3 g of adipic acid and 9.8 g of 6-hydroxcaproic acid, both of which are summed as 17.1 g. Compared with Example 1, the sum of obtained adipic acid (20.9 g) and 6-hydroxycaproic acid (0.33 g) is 21.26 g in total, which is obviously more than products (17.1 g in total) obtained in Comparative Example 1; further, adipic acid is generated in Example 1 at higher proportion than that in Comparative Example 1.

Example 2

Take 50 g of the crude concentrates obtained in Example 1 for use in the following esterification and distillation. Conduct esterification under ambient pressure in a 500-ml reaction glass bottle installed with a reflux condenser for cooling purpose by means of cold water. Put methanol (100 g), the crude concentrates (50 g) and monohydrate of p-toluenesulfonic acid (0.5 g) used as a catalyst into the reaction bottle for proceeding the first-stage esterification at temperature 80° C. for two hours; then, remove the reflux condenser and continuously heat the reaction mixture to evaporate non-reacted methanol and water produced from the reaction. Subsequently, perform the second-stage esterification, and raise the reaction temperature to 110° C. Slowly add 200 g of methanol into the reaction bottle for 4 hours, with the reaction temperature being maintained at 110° C. After addition of methanol is completed, the reaction mixture is heated continuously to evaporate non-reacted methanol and water produced from the reaction; this allows to obtain 53.5 g yield of crude $C_4$–$C_6$ dimethyl dicarboxylates. Analyze the obtained dimethyl dicarboxylates by using gas chromatography, and calculate esterification rates of components thereof as listed in Table 3.

TABLE 3

| Component | Wt. % | Esterification rate (%) |
| --- | --- | --- |
| Dimethyl succinate | 14.13% | 85.6% |
| Dimethyl glutarate | 27.68% | 89.3% |
| Dimethyl adipate | 32.64% | 86.1% |

Calculation of Esterification Rate

Dimethyl succinate (%)=[(53.5 g×14.13%)/146.14]/[(50 g×14.27%)/118.09]×100=85.6%

Dimethyl glutarate (%)=[(53.5 g×27.68%)/160.71]/[(50 g×27.36%)/132.11]×100=89.3%

Dimethyl adipate (%)=[(53.5 g×32.64%)/174.19]/[(50 g×34.03%)/146.14]×100=86.1%

Take 50 g of the crude dimethyl dicarboxylates into a 250-ml distillation bottle, and conduct distillation under 30 mmHg pressure. Collect distillate from 110° C. to 190° C. of temperature, and thus obtain 35.1 g of transparent mixed $C_4$–$C_6$ dimethyl dicarboxylates with high purity. Analyze the obtained dimethyl dicarboxylates by using gas chromatography, and calculate component yields thereof as listed in Table 4.

TABLE 4

| Component | Wt. % | Yield % |
| --- | --- | --- |
| Dimethyl succinate | 17.93% | 89.1% |
| Dimethyl glutarate | 37.58% | 95.3% |
| Dimethyl adipate | 41.61% | 89.5% |

Example 3

Take 120 g of the organic phase (same as the raw material used in Example 1) to proceed a two-step reaction composed of oxidation and conversion, which reaction is performed in a batch manner under ambient pressure. Firstly, conduct the first-step reaction by adding a 50% aqueous solution of nitric acid (360 g) and a 35% aqueous solution of hydrogen peroxide (10 g) into a two-liter reaction bottle. Then, slowly add the above organic phase (120 g) into the bottle with stirring continuously, which addition takes 30 minutes at temperature of 50° C. In the meantime, a weight ratio of the organic phase to nitric acid solution is 1/3. After addition, the reaction is continued for two more hours. Subsequently, conduct the second-step reaction by raising temperature to 70° C., allowing the reaction to be proceeded for two hours. After completing the two-step reaction, a concentration process is performed as follows.

Concentration is performed with a two-stage process. In the first-stage concentration, when temperature reaches about 120° C., introduce steam to the reaction mixture for removing free nitric acid. Then stop steaming, and continuously raise concentration temperature to 140° C., so as to completely decompose all nitrocompounds in the reaction mixture. Complete concentration, and obtain 63.49 g yield of crude concentrates of $C_4$–$C_6$ dicarboxylic acids, with components thereof being analyzed as listed in Table 5.

TABLE 5

| Component | Wt. % | Weight of dicarboxylic acids (including 6-hydroxylcaproic acid) contained in 62.49 g crude concentrates |
| --- | --- | --- |
| Formic acid | 0 | |
| Acetic acid | 0 | |
| Butyric acid | 0 | |
| Valeric acid | 0.21% | |
| Caproic acid | 0 | |
| Succinic acid | 13.48% | 8.42 g |
| Glutaric acid | 26.48% | 16.55 g |
| Adipic acid | 32.76% | 20.47 g |
| 6-hydroxylcaproic acid | 0.55% | 0.34 g |
| Water | 0 | |
| $NO_3^-$ | 0.07% | |
| Others | 26.45% | |
| Total | 100% | 45.78 g |

In view of the above results, weight of dicarboxylic acids (including 6-hydroxylcaproic acid) changes from 31.38 g contained in the original organic phase to 45.78 g in the crude concentrates obtained in this example of the invention, by weight increase of 14.4 g and increase rate of 45.89%, with 6-hydroxylcaproic acid being significantly decreased in weight, so that the obtained crude concentrates mainly comprise $C_4$–$C_6$ dicarboxylic acids.

Example 4

Take 50 g of the crude concentrates obtained in Example 3 for use in the following esterification and distillation. Add methanol (150 g) and the crude concentrates (50 g) into a 500-ml high-pressure reactor, and close an outlet of the reactor for starting the first-stage esterification at 90° C. After proceeding the reaction for two hours, open the outlet and continue heating to evaporate non-reacted methanol and water produced from the reaction Subsequently, proceed the second-stage esterification, and raise temperature to 120° C. Slowly add 200 g of methanol into the reactor under 120° C. and pressure around 1.2 kg/cm² for about four hours. After addition, keep heating the reaction to drive out non-reacted methanol and water produced from the reaction, and thus obtain 54.1 g of crude $C_4$–$C_6$ dimethyl dicarboxylates.

Analyze the obtained dimethyl dicarboxylates by using gas chromatography, and calculate esterification rates of components thereof as listed in Table 6.

TABLE 6

| Component | Wt. % | Esterification rate (%) |
| --- | --- | --- |
| Dimethyl succinate | 13.29% | 86.2% |
| Dimethyl glutarate | 26.38% | 88.9% |
| Dimethyl adipate | 31.51% | 87.3% |

Take 50 g of the above crude dimethyl dicarboxylates into a 250-ml distillation bottle under 30 mmHg pressure. Collect distillate from 110° C. to 190° C. in temperature, and obtain 34.0 g of transparent mixed $C_4$–$C_6$ dimethyl dicarboxylates with high purity.

Analyze the obtained dimethyl dicarboxylates by using gas chromatography, and calculate component yields thereof as listed in Table 7.

TABLE 7

| Component | Wt. % | Yield (%) |
| --- | --- | --- |
| Dimethyl succinate | 18.29% | 93.58% |
| Dimethyl glutarate | 37.40% | 96.41% |
| Dimethyl adipate | 41.87% | 90.36% |

Example 5

Reaction of this example is continuously carried out at ambient pressure, and uses a raw material of the same organic phase as that in Example 1. Prepare a 40% aqueous solution of nitric acid. Continuously input the organic phase and nitric acid solution simultaneously into a two-step oxidation and conversion reactor by using a ration pump, so as to control a weight ratio of the organic phase to nitric acid at 1/7. The first-step reaction is proceeded for one hour at temperature of 50° C., whereas the second-step reaction is run at temperature 70° C. with reaction time of one hour. Collect the resulting reaction mixture obtained from the second-step reaction, and concentrate the obtained reaction mixture, in which concentration is performed in a batch manner as same as in Example 1, whereby 62.89 g yield of crude concentrates mainly comprising $C_4$–$C_6$ dicarboxylic acids is obtained. By component analysis, weight of dicarboxylic acids (including 6-hydroxylcaporic acid) contained in the crude concentrates is 48.73 g, which is increased by 17.35 g in weight and 55.29% in rate, as compared to 31.38 g of dicarboxylic acids (including 6-hydroxylcaporic acid) contained in the original organic phase.

Example 6

Take 50 g of the crude concentrates obtained from Example 5 for use in the following esterification and distillation, wherein materials are continuously fed into an esterification reactor. Firstly, add 100 g of methanol into the first-stage esterification reactor. Then, continuously feed methanol and the crude concentrates simultaneously into the reactor by using a ration pump, with a weight ratio of methanol to the crude concentrates being controlled at 2/1. The first-stage esterification is proceeded at 80° C. for one hour. Subsequently, the reaction mixture flows to the second-stage esterification reactor with temperature being raised to 130° C., and methanol is fed into the reactor by a ration pump with a weight ratio of methanol to the crude concentrates being maintained at 3/1, allowing the reaction to be proceeded for one hour. Keep heating to evaporate non-reacted methanol and water produced from the reaction, and thus obtain 55.1 g yield of crude $C_4$–$C_6$ dimethyl dicarboxylates. Analyze the obtained dimethyl dicarboxylates by using gas chromatography, and calculate esterification rates of components thereof as listed in Table 8.

TABLE 8

| Component | Wt. % | Esterification rate (%) |
| --- | --- | --- |
| Dimethyl succinate | 14.1% | 87.5% |
| Dimethyl glutarate | 27.3% | 89.1% |
| Dimethyl adipate | 30.2% | 88.1% |

What is claimed is:

1. A method for recovering and producing $C_4$–$C_6$ dicarboxylates from an alkaline waste solution generated in a caprolactam preparation process, comprising the steps of:
    (1) adding sulfuric acid to the alkaline waste solution generated from the caprolactam preparation process to adjust a pH value thereof to a pH of less than 7, separating the alkaline waste solution into an aqueous phase and an organic phase; adding nitric acid to the organic phase for oxidizing and converting valuable substances selected from adipic acid, 6-hydroxycaproic acid, saponified esters or ketones of cyclohexanol, and $C_4$–$C_6$-lactones, contained in the organic phase into dicarboxylic acids, thereby obtaining an oxidized reaction mixture containing dicarboxylic acids;
    (2) introducing the oxidized reaction mixture obtained from the step (1) into a two-stage concentration apparatus; in first-stage concentration, distilling out low boiling-point monocarboxylic acids and nitric acid; in second-stage concentration, the concentration is carried out at a temperature of 120° C. to 200° C. and an absolute pressure of 0.5 to 2.0 kg/cm$^2$, so as to obtain crude concentrates mainly containing $C_4$–$C_6$ dicarboxylic acids;
    (3) adding $C_1$–$C_4$ alkyl alcohol to the crude concentrates mainly containing $C_4$–$C_6$ dicarboxylic acids obtained from the step (2), and proceeding two-stage esterification, whereby half-esterified intermediates are obtained in first-stage esterification, and crude dicarboxylates ore obtained in second-stage esterification; and
    (4) distilling the crude dicarboxylates obtained from the step (3), so as to get single-species dicarboxylates or a mixture of dicarboxylates.

2. The method of claim 1, wherein in the step (1), at least one oxidant other than nitric acid selected from the group consisting of hydrogen peroxide, perchloric acid, and potassium permanganate, is added to the organic phase.

3. The method of claim 1, wherein concentration of nitric acid is 10 to 90%.

4. The method of claim 1, wherein a weight ratio of nitric acid to the organic phase is 0.5 to 30:1.

5. The method of claim 2, wherein the oxidant is added in a ratio of 0 to 5% relative to nitric acid by weight.

6. The method of claim 1, wherein oxidation and conversion of the step (1) are performed under conditions including: at least one reaction stage, reaction temperature of a range from 10 to 150° C., and reaction mixture flowing from first to last reaction stage with the reaction temperature being increased gradually at stage intervals of 5 to 30° C., reaction time for each stage being set as 5 minutes to 4 hours, and reaction pressure being absolute pressure 0.5 to 2 kg/cm$^2$.

7. The method of claim 1, wherein in the step (2), the first-stage concentration is performed at a temperature of 50 to 120° C. and an absolute pressure of 0.2 to 1.5 kg/cm², the second-stage concentration is carried out at a temperature of 120 to 200° C and an absolute pressure of 0.5 to 2.0 kg/cm².

8. The method of claim 1, wherein the $C_1$–$C_4$ alkyl alcohol used in the step (3) is selected from a group consisting of methanol, ethanol, propanol and butanol.

9. The method of claim 1, wherein a weight ratio of the $C_1$–$C_4$ alkyl alcohol to the crude concentrates of dicarboxylic acids is 1–15:1.

10. The method of claim 8, wherein a weight ratio of the $C_1$–$C_4$ alkyl alcohol to the crude concentrates of dicarboxylic acids is 1–15:1.

11. The method of claim 1, wherein a catalyst is added in the step (3), and selected from a group consisting of sulfuric acid, phosphoric acid, nitric acid, alkanesulfonic acids, benzenesulfonic acid and cation exchange resin.

12. The method of claim 11, wherein the catalyst is added in an amount of 0 to 5%.

13. The method of claim 1, wherein in the step (3), the first-stage esterification is performed at a temperature of 40 to 120° C., an absolute pressure of 0.2 to 1.2 kg/cm², and esterification time of 0.5 to 8 hours; and the second-stage esterification is carried out at a temperature of 80 to 200° C., an absolute pressure of 0.8 to 2.5 kg/cm², and esterification time of 0.5 to 8 hours.

14. The method of claim 1, wherein a distillation apparatus used in the step (4) is a tray or packed distillation apparatus.

15. The method of claim 13, wherein distillation of the step (4) is performed by using 10 to 100 trays theoretically, and under absolute pressure of 0.02 to 1.0 kg/cm² and temperature of 70 to 250° C.

16. The method of claim 1, comprising the steps of:

(1) adding sulfuric acid to the alkaline waste solution generated from the caprolactam preparation process to adjust a pH value thereof to a pH of less than 7, and separating the alkaline waste solution into an aqueous phase and an organic phase; adding nitric acid of 10 to 90% concentration to the organic phase in a weight ratio of nitric acid to the organic phase at 0.5 to 30:1, and oxidizing and converting valuable substances selected from adipic acid, 6-hydroxycaproic acid, saponified esters or ketones of cyclohexanol, and $C_4$–$C_6$-lactones contained in the organic phase into dicarboxylic acids, thereby obtaining an oxidized reaction mixture containing dicarboxylic acids;

(2) introducing the oxidized reaction mixture obtained from the step (1) into a two-stage concentration apparatus, wherein first-stage concentration is performed at a temperature of 50 to 120° C. and an absolute pressure of 0.2 to 1.5 kg/cm², and second-stage concentration is carried out at a temperature of 120 to 200° C. and an absolute pressure of 0.5 to 2.0 kg/cm², so as to obtain crude concentrates mainly containing $C_4$–$C_6$ dicarboxylic acids;

(3) adding $C_1$–$C_4$ alkyl alcohol to the crude concentrates mainly containing $C_4$–$C_6$ dicarboxylic acids obtained from the step (2), and proceeding two-stage esterification, wherein first-stage esterification is performed at temperature of 40 to 120° C., absolute pressure of 0.2 to 1.2 kg/cm², and esterification time of 0.5 to 8 hours; and second-stage esterification is carried out at temperature of 80 to 200° C., absolute pressure of 0.8 to 2.5 kg/cm², and esterification time of 0.5 to 8 hours, so as to obtain crude dicarboxylates; and (4) introducing the crude dicarboxylates obtained from the step (3) into a tray- or packed distillation tower for performing distillation by using 10 to 100 trays theoretically, and under absolute pressure of 0.02 to 1.0 kg/cm² and temperature of 70 to 250° C., so as to get single-species dicarboxylates or a mixture of dicarboxylates.

* * * * *